United States Patent [19]
Devincenzo

[11] 4,439,149
[45] Mar. 27, 1984

[54] VERTICALLY-INDEXED POSTERIOR BITE PLATES

[76] Inventor: John Devincenzo, 1312 Garden St., San Luis Obispo, Calif. 93401

[21] Appl. No.: 418,670

[22] Filed: Sep. 16, 1982

[51] Int. Cl.³ .............................................. A61C 7/00
[52] U.S. Cl. ...................................................... 433/6
[58] Field of Search ................................... 433/7, 19, 6

[56] References Cited

U.S. PATENT DOCUMENTS 2,708,314  5/1955  Schwartz ............................ 433/197

FOREIGN PATENT DOCUMENTS 1252156 12/1960 France .................................... 433/19

Primary Examiner—Robert Peshock
Attorney, Agent, or Firm—Daniel C. McKown

[57] ABSTRACT

A removable orthodontic appliance that includes an upper plate and a lower plate, the plates being unattached to each other but contacting each other on portions of their surfaces called indexing planes, which are oriented vertically. The tendency of the lower jaw to retract is opposed by the indexing planes of the upper plate which are located on the molars. The indexing planes of the upper plate bear against the indexing planes of the lower plate and thereby maintain the jaw in a jutting-forward position while not interfering with the opening and closing of the jaw that is necessary for normal eating, speaking and sleeping. The appliance of the present invention can be worn 24 hours a day by the patient and operates continuously while in place to maintain the condyles in desired positions.

2 Claims, 9 Drawing Figures

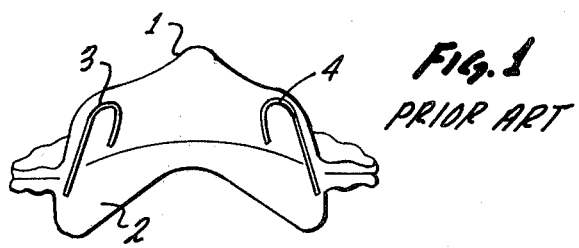
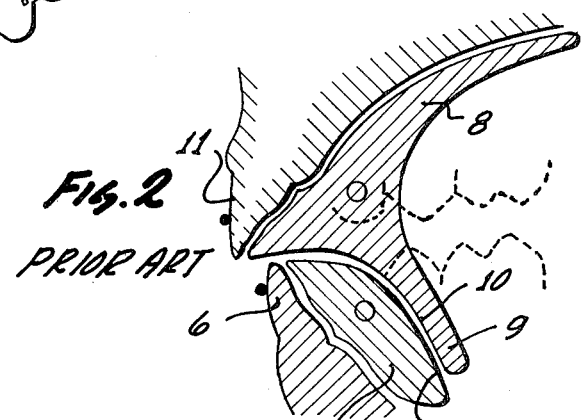
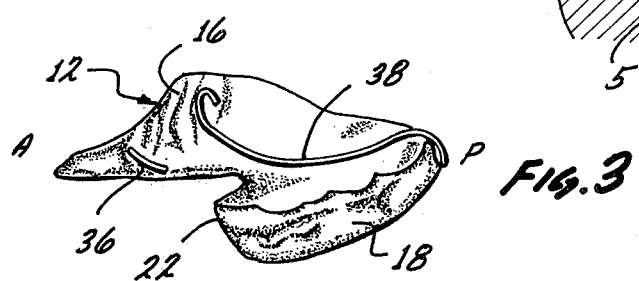
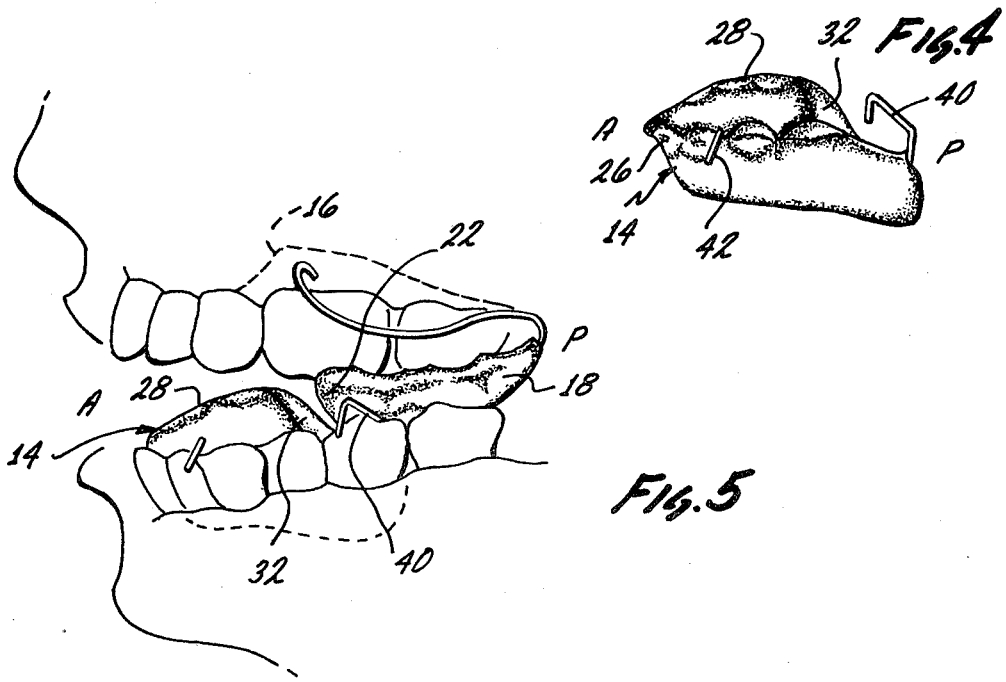

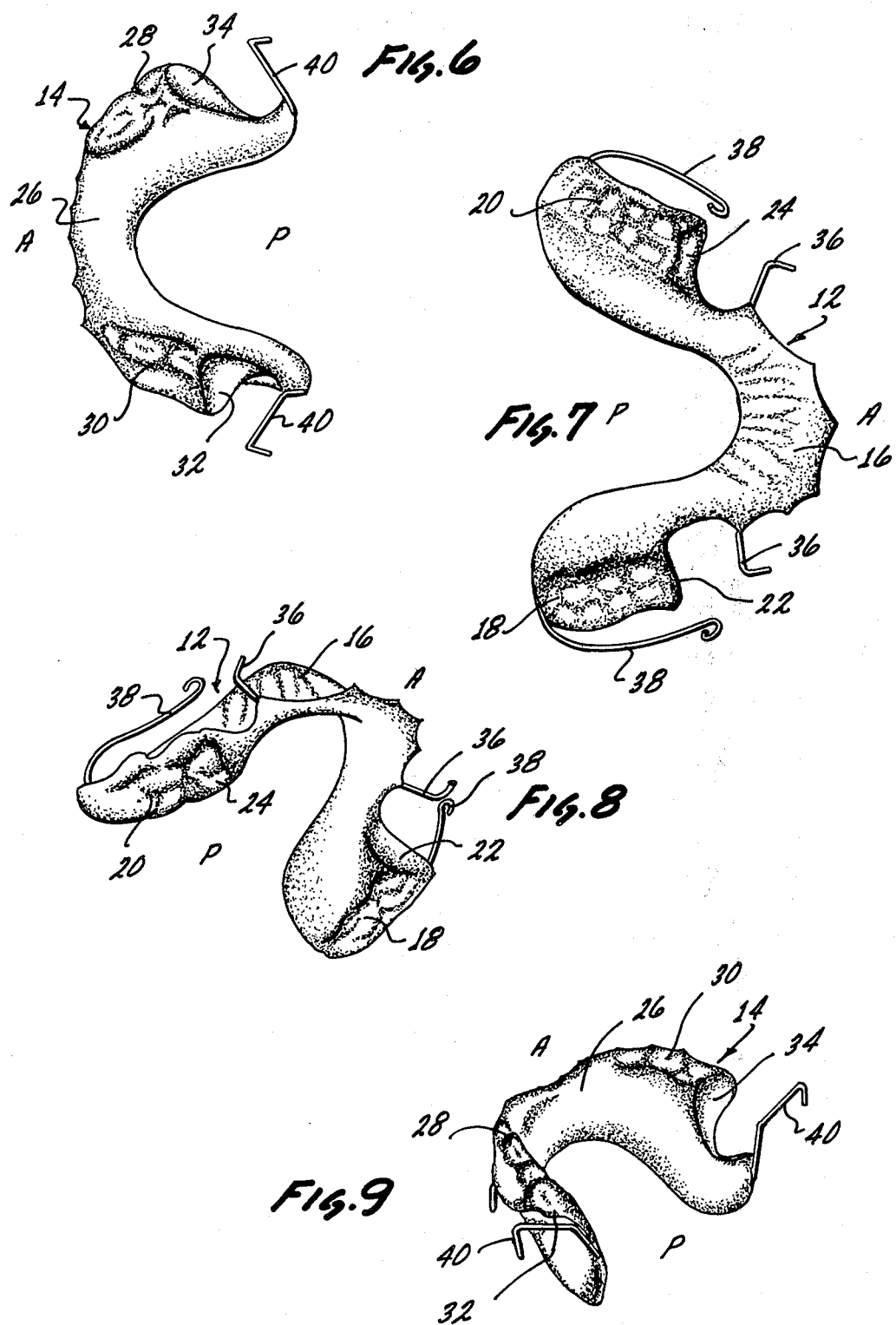

VERTICALLY-INDEXED POSTERIOR BITE PLATES

BACKGROUND OF THE INVENTION

1. Field of the Invention

The present invention is in the field of orthodontics and more specifically is a removable orthodontic appliance that employs vertically-indexed posterior bite plates for correcting Class II Division 1 malocclusions primarily.

2. The Prior Art

An appliance known as the U-bow activator of Karwetzky has been used to correct Class II Division 1 malocclusions and certain other malocclusions. The appliance, shown in FIG. 1, consists of maxillary and mandibular active plates, 1 and 2 respectively, joined by two U-bows 3, 4 of heavy wire. The plates cover the occlusal surfaces of all the teeth as well as parts of the gums and touches the tongue along their lingual aspects. The position of the lower plate relative to the upper plate is controlled by the U-bow and the lower plate is moved forward relative to the upper plate by squeezing the sides of the U-bow together.

Far from having indexing planes comparable to those of the present invention, the Karwetzky appliance has smooth planar horizontal opposing surfaces on the upper and lower plates.

Because the wire used in forming the U-bow must be stiff enough to oppose any tendancy of the lower jaw to move posteriorly, the wire and the plates themselves tend to be bulky. Patient adaptation to this appliance is difficult, and while it is being worn normal speaking and eating activities are impossible.

Full time wear is impossible. Sometimes, when the patient attempts to sleep with the appliance in place, the mandibular teeth will drop behind the mandibular plate thereby rendering the device ineffective.

In the Karwetzky appliance, unlike the present invention, when the lower jaw tries to move posteriorly, it pulls the connected plates posteriorly, and this tendancy is opposed mainly by the maxillary anterior teeth which are thereby moved distally. This is undesirable because those teeth are the least able to withstand such a force. In contrast, in the appliance of the present invention, the posterior pulling of the lower jaw is opposed mainly by the upper posterior teeth which are more able to withstand the force.

Another appliance sometimes used for correcting Class II Division 1 malocclusions is known as the Schwartz double plate. This appliance, shown in FIG. 2, includes a lower plate 5 that fits behind the incisors 6. This lower plate includes a distal surface 7 that slopes downwardly posteriorly. The upper plate 8 fits behind the upper incisors 11 and includes a downwardly and distally extending portion 9 that lies behind the rear surface of the lower plate. The front surface 10 of this downwardly and distally extending portion slides along the posterior surface 7 of the lower plate. As the lower jaw is closed, it is forced forward as the inclined distal surface 7 of the lower plate rides up along the downwardly and posteriorly extending portion 9 of the upper plate. In a preferred embodiment of the double plate, the downwardly and posteriorly extending portion 9 of the upper plate is replaced by adjustable guide elements formed of wire.

An obvious defect of this type of appliance is that as the mandible opens, as in sleep, the lower plate 5 slides downwardly and posteriorly along the upper plate thereby rendering the appliance ineffective during sleep. Also, the patient cannot eat or speak normally with the appliance in place.

In contrast to the appliance of the present invention, in the double plate appliance, the main force is applied against the lower incisors, tending to tip them forward.

In summary, none of the appliances of the known prior art is fully satisfactory, and the need for an improved appliance was recognized by the present inventor.

SUMMARY OF THE INVENTION

The present invention overcomes the problems associated with prior art devices by providing a removable orthodontic appliance that includes vertically-indexed posterior bite plates. The appliance can be worn continuously by the patient 24-hours a day, and it permits the patient to eat, sleep, talk, and chew in a generally normal manner.

The appliance of the present invention allows the practitioner to place the jaw in a constant precise position which can then be maintained by the patient. The appliance, in one of its uses, can stimulate the mandible to change selectively faster than the maxilla by providing conscious and subconscious control of mandibular position. In another of its uses, the appliance can precisely control condylar position for the treatment of TMJ disorders.

The appliance includes a maxillary part and a a mandibular part. The maxillary part is anchored to the upper teeth and includes an upper bite plate that generally covers the occlusal surfaces of the upper posterior molars. This upper bite plate terminates at its anterior end in a substantially plane surface that is generally perpendicular to the plane of the occlusal surfaces and perpendicular to the direction of the row of upper teeth.

Likewise, the lower part is anchored to the lower teeth and includes a lower bite plate that generally covers the occlusal surfaces of the lower pre-molars, that presses forward against the lower incisors and lower gum, and that terminates at its posterior end in a substantially plane surface that is generally perpendicular to the plane of the occlusal surfaces and perpendicular to the direction of the row of lower teeth.

The appliance can also be constructed in just the reverse fashion: namely, the maxillary vertical plane can be anteriorly positioned just distal to the cuspids and the mandibular vertical plane and bite plate can occupy the posterior area. The appliance used in this way could serve to position the condyles distally in the glenoid fossae.

The vertical plane surfaces of the upper part and of the lower part are in contact when the appliance is worn. The vertical plane surface of the lower bite plate is prevented from moving posteriorly by the vertical plane surface of the upper bite plate. As the jaws open and close, the lower plane surface slides against the upper plane surface. The plane surface of the upper part can, if desired, be constructed to hold the lower jaw in a protrusive position.

The height of the plane surface can be a significant variable in certain conditions but is frequently about five millimeters. The plane surfaces of the maxillary and mandibular parts will remain engaged so long as the opening movement of the jaw does not exceed five millimeters at the location of the plane surfaces. But, because the plane surfaces are located closer to the hinge of the jaw than are the incisors, the anterior opening required to disengage the parts will be two to four times greater than the five millimeters. This helps maintain the patient in a protrusive mandibular position when eating and talking and sleeping.

It is normal for a person to open his jaw slightly while sleeping. When a person wearing the appliance of the present invention engages in this normal activity, the height of the plane surfaces prevents the lower part from becoming disengaged from the upper part and from retracting. Because the appliance of the present invention can be worn and is effective while the patient is sleeping, the appliance can produce results more rapidly than appliances that cannot be worn 24 hours per day, and the results are of a different character.

As viewed from above or below, the teeth are arranged along an arch that diverges in the posterior. The plane surfaces are generally perpendicular to this arch and extend generally in the buccal-lingual direction; hence the plane surfaces, if extended, would intersect along a vertical line located in the back of the mouth. This provides a self-centering of the lower part with respect to the upper part as the lower plane surfaces slide against the upper plane surfaces, thereby imparting lateral stability to the lower part.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective posterior view of the Karwetzky U-bow activator appliance known in the prior art;

FIG. 2 is a side cross sectional view in a sagital plane of the double plate appliance known in the prior art;

FIG. 3 is a side elevation view of the upper plate of the appliance in a preferred embodiment of the present invention;

FIG. 4 is a side elevation view of the lower plate of the appliance of a preferred embodiment of the present invention;

FIG. 5 is a side elevation view of the appliance of a preferred embodiment of the present invention installed in a mouth;

FIG. 6 is a plan view of the lower plate of the appliance in a preferred embodiment of the present invention;

FIG. 7 is a plan view of the upper plate of the appliance in a preferred embodiment of the present invention;

FIG. 8 is a perspective view from below and beside the upper plate of the appliance in a preferred embodiment of the present invention; and FIG. 9 is a perspective view from above and behind the lower plate of the appliance in a preferred embodiment of the present invention.

DETAILED DESCRIPTION OF THE PREFERRED EMBODIMENT

Turning now to the drawings, in which like parts are denoted by the same reference numeral throughout, it should be noted that the FIGS. 3-9 all relate to the same preferred embodiment of the present invention. The letters A and P on the Figures denote the anterior and posterior regions. The appliance of the present invention includes an upper plate 12 and a lower plate 14.

The upper plate 12 includes a central portion 16 that in use lies against the lingual surface of the maxillary gingival process for stability. The central portion 16 also serves to interconnect the left and right bite plates 18, 20. These plates extend laterally from the lower portion of the central portion 16 to cover a portion of the occlusal surfaces of the maxillary molars, as perhaps best seen in FIG. 5. The left and right bite plates 18, 20 are shaped to include at their anterior ends the substantially planar indexing planes 22, 24.

Similarly, the lower plate 14 includes a central portion 26 that in use lies against the lingual surface of the mandibular gingival process and that interconnects a left bite plate 28 and a right bite plate 30. These bite plates 28, 30 cover the lower bicuspids and incisors and a portion of the molars. The left and right bite plates 28, 30 are shaped to include at their posterior ends the indexing planes 32, 34 respectively.

The upper plate 12 includes the pairs of wires 36 and 38 that are used to fix and to hold the upper plate to the upper teeth. Similarly, the lower plate 14 includes the pairs of wires 40 and 42 which serve the same purpose for the lower plate. The design of these wires as well as their locations vary with individual adaptations.

The upper plate 12 and the lower plate 14 are installed in the mouth in the manner shown in FIG. 5. Note that the left indexing plane 22 of the upper plate 12 lies against the left indexing plane of the lower plate 14. Likewise, the right indexing plane of the upper plate 12 lies against the right indexing plane 34 of the lower plate 14. The indexing planes 22, 24 of the upper plate 12 prevent rearward movement of the lower plate 14, thereby maintaining the lower jaw in a thrust-forward position.

The presence of the bite plates 18, 20, 28, 30 keeps the upper and lower teeth separated, thereby maintaining the jaw in a slightly opened position. The bite plates also function as the occlusal surfaces during eating. These occlusal surfaces are generally specifically indexed into the opposing natural teeth.

Thus, when the appliance of the present invention is used to correct a Class II malocclusion, the mandible is maintained in a thrust-forward and slightly opened position, the combined effect of which is to promote growth and/or adaptation of the jaw in the downward and forward directions. In other applications, such as use in treatment of TMJ disorders, it serves only to reposition the condyle in the glenoid fossa.

From FIG. 5 it is seen that if the indexing planes 22, 32 were to slope forward and upward, the lower plate 14 would have a tendency to slide down the indexing plane, as was discussed in connection with the appliance shown in FIG. 2. On the other hand, if the indexing planes 22, 32 were to slope upwardly distally, then the lower plate 14 would be latched to the upper plate 12, and this would interfere with chewing and would complicate opening of the jaw. Therefore, in accordance with the preferred embodiment of the present invention, the indexing planes 22, 32 must be substantially vertical to avoid both of these undesired effects. In this context, by vertical is meant that all points on the plane are substantially equidistant from the hinge axis of the jaw. It is for this reason that the appliance of the present invention is referred to as being vertically-indexed.

The appliance of the present invention has been tested clinically with excellent results and with good patient acceptance.

Thus, there has been described a removable orthodontic appliance including vertically-indexed upper and lower plates. Each of the plates includes a pair of substantially vertical planes, and when the device is in use, these planes are in contact. The indexing planes maintain the lower jaw in a jutting-forward position for the correction of Class II malocclusions and require only minimal conscious effort on the part of the patient.

The foregoing detailed description is illustrative of a preferred embodiment of the invention, and it is to be understood that additional embodiments thereof will be obvious to those skilled in the art. The embodiment described herein together with those additional embodiments are considered to be within the scope of the invention.

What is claimed is:

1. An orthodontic appliance comprising:
   an upper bite plate including a vertical anterior-facing indexing plane, said upper bite plate secured to the upper posterior teeth;
   a lower bite plate including a vertical posterior-facing indexing plane, said lower bite plate bearing against the lower front teeth, said vertical posterior-facing indexing plane contacting said vertical anterior-facing indexing plane to prevent retraction of said lower bite plate and sliding on said vertical anterior-facing indexing plane as the jaw opens and closes.

2. In an orthodontic appliance of the type having an upper bite plate and a lower bite plate, the improvement comprising:
   a vertical anterior-facing index surface on the upper bite plate; and,
   a vertical posterior-facing index surface on the lower bite plate, positioned to face said vertical anterior-facing index surface of the upper bite plate for maintaining the upper bite plate and the lower bite plate in a fixed anterio-posterior relationship and simultaneously for enabling vertical movement of the lower bite plate with respect to the upper bite plate as the jaw opens and closes.

* * * * *